United States Patent
Jang et al.

(10) Patent No.: US 9,008,263 B2
(45) Date of Patent: Apr. 14, 2015

(54) APPARATUS AND METHOD FOR IMAGING BREAST

(75) Inventors: Kwang Eun Jang, Busan (KR); Jong Ha Lee, Hwaseong-si (KR); Dong Goo Kang, Suwon-si (KR); Young Hun Sung, Hwaseong-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 920 days.

(21) Appl. No.: 13/067,790

(22) Filed: Jun. 27, 2011

(65) Prior Publication Data

US 2012/0014504 A1 Jan. 19, 2012

(30) Foreign Application Priority Data

Jul. 19, 2010 (KR) .................. 10-2010-0069569

(51) Int. Cl.
*A61B 6/04* (2006.01)
*A61B 6/00* (2006.01)

(52) U.S. Cl.
CPC ............... *A61B 6/502* (2013.01); *A61B 6/405* (2013.01); *A61B 6/482* (2013.01); *A61B 6/5235* (2013.01); *A61B 6/5241* (2013.01)

(58) Field of Classification Search
CPC ...... A61B 6/025; A61B 6/0414; A61B 6/482; A61B 6/502
USPC ........... 378/22, 25, 26, 37, 5, 16, 98.9, 98.11, 378/98.12
See application file for complete search history.

(56) References Cited

U.S. PATENT DOCUMENTS

| | | | | |
|---|---|---|---|---|
| 5,872,828 A * | 2/1999 | Niklason et al. | ................ | 378/23 |
| 5,930,327 A | 7/1999 | Lin | | |
| 6,173,034 B1 * | 1/2001 | Chao | ................ | 378/37 |
| 6,748,047 B2 * | 6/2004 | Gonzalez Trotter et al. | ... | 378/62 |
| 6,751,285 B2 * | 6/2004 | Eberhard et al. | ................ | 378/37 |
| 6,882,700 B2 * | 4/2005 | Wang et al. | ................ | 378/37 |
| 7,110,490 B2 * | 9/2006 | Eberhard et al. | ................ | 378/23 |
| 7,245,694 B2 * | 7/2007 | Jing et al. | ................ | 378/37 |
| 7,356,113 B2 * | 4/2008 | Wu et al. | ................ | 378/27 |
| 7,431,500 B2 * | 10/2008 | Deych et al. | ................ | 378/207 |
| 7,453,979 B2 * | 11/2008 | Sendai | ................ | 378/23 |
| 7,463,713 B2 * | 12/2008 | Mertelmeier | ................ | 378/22 |
| 7,545,907 B2 * | 6/2009 | Stewart et al. | ................ | 378/37 |
| 7,693,254 B2 * | 4/2010 | Muller et al. | ................ | 378/37 |
| 7,697,661 B2 * | 4/2010 | Souchay et al. | ................ | 378/37 |
| 7,751,528 B2 * | 7/2010 | Zhou et al. | ................ | 378/37 |
| 7,778,388 B2 * | 8/2010 | Sendai | ................ | 378/22 |

(Continued)

FOREIGN PATENT DOCUMENTS

| | | |
|---|---|---|
| JP | 2004-173856 | 6/2004 |
| JP | 2008-054831 | 3/2008 |

(Continued)

*Primary Examiner* — Allen C. Ho
(74) *Attorney, Agent, or Firm* — Staas & Halsey LLP (57) ABSTRACT

An apparatus and method for imaging a breast are provided. The apparatus includes an X-ray emission unit that emits an X-ray of a first energy spectrum and an X-ray of a second energy spectrum from above a first region of a breast and emits an X-ray of a third energy spectrum from above a second region of the breast different from the first region of the breast; an X-ray detection unit that generates a plurality of image frames related to the breast by detecting the X-rays emitted and passed through the breast; and an image generation unit that generates image data related to the breast by combining the plurality of image frames.

22 Claims, 5 Drawing Sheets

(56) References Cited

U.S. PATENT DOCUMENTS

| | | | |
|---|---|---|---|
| 7,831,296 B2 * | 11/2010 | DeFreitas et al. | 600/427 |
| 7,835,491 B2 * | 11/2010 | Fischer et al. | 378/37 |
| 7,853,064 B2 * | 12/2010 | Bernard et al. | 382/132 |
| 7,881,513 B2 * | 2/2011 | Bernard et al. | 382/128 |
| 8,036,442 B2 * | 10/2011 | Bernard et al. | 382/132 |
| 8,041,094 B2 * | 10/2011 | Bernard et al. | 382/131 |
| 8,149,987 B2 * | 4/2012 | Ogura et al. | 378/37 |
| 8,363,050 B2 * | 1/2013 | Ludwig et al. | 345/419 |
| 8,477,901 B2 * | 7/2013 | Dolazza et al. | 378/22 |
| 8,576,988 B2 * | 11/2013 | Lewalter et al. | 378/126 |
| 2006/0269040 A1 | 11/2006 | Mertelmeier | |
| 2010/0034450 A1 * | 2/2010 | Mertelmeier | 382/131 |

FOREIGN PATENT DOCUMENTS

| | | |
|---|---|---|
| KR | 10-2004-0047561 | 6/2004 |
| KR | 10-2006-0053553 | 5/2006 |

\* cited by examiner

APPARATUS AND METHOD FOR IMAGING BREAST

CROSS-REFERENCE TO RELATED APPLICATIONS

This application claims the priority benefit of Korean Patent Application No. 10-2010-0069569, filed on Jul. 19, 2010, in the Korean Intellectual Property Office, the disclosure of which is incorporated herein by reference.

BACKGROUND

1. Field

Embodiments of the following description relate to an apparatus and method for imaging breast.

2. Description of the Related Art

Recently, occurrence of breast cancer is gradually increasing due to the entry of women in public affairs, a westernized diet, a low birth rate, and so forth. An incidence rate of breast cancer is especially high among young people. Accordingly, women's knowledge about the necessity of breast cancer examination is increasing.

Methods for breast cancer examination include a breast imaging examination and a breast ultrasound. The breast imaging examination is performed using a mammography which is an X-ray imaging device, a full field digital mammography (FFDM) employing a digital flat panel, and so forth.

When microcalcifications (MC) or masses shown in a breast image generated by those devices, a doctor may diagnose that there is the possibility of breast cancer. That is, images of the MCs or masses need to be accurately generated by the devices for an accurate diagnosis of breast cancer. However, it is limited to accurately show in an image both MCs and masses with a limited dose of irradiation due to different characteristics of the MCs and the masses.

According to a related-art mammography, tissues in a breast are compressed and 2D-projected, thereby obtaining an image. Although an image accurately shows MCs, the accuracy of images of the masses is relatively low. To this end, digital tomography is used to increase the accuracy of mass detection.

However, since the digital tomography images a breast several times at different angles, a relatively high dose of X-rays is irradiated to a patient. In addition, the digital tomography generates an image at a rate of 2 frames per second at most to produce a high resolution image.

SUMMARY

According to an aspect of one or more embodiments, there is provided an apparatus for imaging a breast, including an X-ray emission unit that emits an X-ray of a first energy spectrum and an X-ray of a second energy spectrum from above a first region of a breast and emits an X-ray of a third energy spectrum from above a second region of the breast different from the first region of the breast, an X-ray detection unit that generates a plurality of image frames related to the breast by detecting the X-rays emitted and passed through the breast, and an image generation unit that generates image data related to the breast by combining the plurality of image frames.

The X-ray emission unit may further emit an X-rays of a fourth energy spectrum and a fifth energy spectrum from above a third region of the breast which is different from the first region of the breast.

The second region of the breast and the third region of the breast may share an overlapping region.

The X-ray detection unit may generate a first image group consisting of a plurality of image frames having a full resolution by detecting X-rays of the first energy spectrum and the second energy spectrum emitted from above the first region of the breast.

The X-ray detection unit may generate a second image group consisting of a plurality of image frames having a low resolution by binning a plurality of pixels corresponding to the X-ray of the third energy spectrum emitted from above the second region of the breast.

The X-ray detection unit may generate a third image group consisting of a plurality of image frames having a full resolution by detecting the X-rays of the fourth energy spectrum and the fifth energy spectrum emitted from above the third region of the breast.

The image generation unit may generate image data related to the breast by combining the plurality of image frames constituting each of the first group, the second group, and the third group generated in the X-ray detection unit.

According to an aspect of one or more embodiments, there is provided a method for imaging a breast, including emitting X-rays of a first energy spectrum and a second energy spectrum from above a first region of a breast, emitting an X-ray of a third energy spectrum from above a second region of the breast different from the first region of the breast, generating a plurality of image frames related to the breast by detecting the X-ray emitted and passed through the breast, and generating image data related to the breast by combining the plurality of image frames.

The method may further include emitting X-rays of a fourth energy spectrum and a fifth energy spectrum from above a third region of the breast, which is different from the first region of the breast.

The second region of the breast and the third region of the breast may share an overlapping region.

The generating of the plurality of image frames may include generating a first image group consisting of a plurality of image frames having a full resolution by detecting the X-rays of the first energy spectrum and the second energy spectrum emitted from above the first region of the breast, generating a second image group consisting of a plurality of image frames having a low resolution by binning a plurality of pixels corresponding to the X-ray of the third energy spectrum emitted from above the second region of the breast, and generating a third image group consisting of a plurality of image frames having a full resolution by detecting X-rays of the fourth energy spectrum and the fifth energy spectrum emitted from above the third region of the breast.

The generating of the image data related to the breast may include generating image data related to the breast by combining the plurality of image frames constituting each of the first image group, the second image group, and the third image group.

The image generation unit may further include an output unit to output an image of the breast based on image data. The output unit may be a display unit to display the image of the breast. The output unit may be a printer which prints the image of the breast.

The method may further include outputting an output image of the breast based on the image data. The output image of the image data may be displayed on a display unit. The output image of the image data may be printed by a printer.

According to another aspect of one or more embodiments, there is provided at least one non-transitory computer readable medium storing computer readable instructions to implement methods of one or more embodiments.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Reference will now be made in detail to embodiments, examples of which are illustrated in the accompanying drawings, wherein like reference numerals refer to the like elements throughout. Detailed descriptions related to well-known functions or configurations will be ruled out in order not to unnecessarily obscure subject matters of the present invention. In addition, the technical terms are used only for explaining a specific exemplary embodiment and may be changed according to user's intention or use in related fields. Therefore, the meaning of the terms is to be defined based on the specification. Like reference numerals in the drawings denote like elements.

Figure 1:
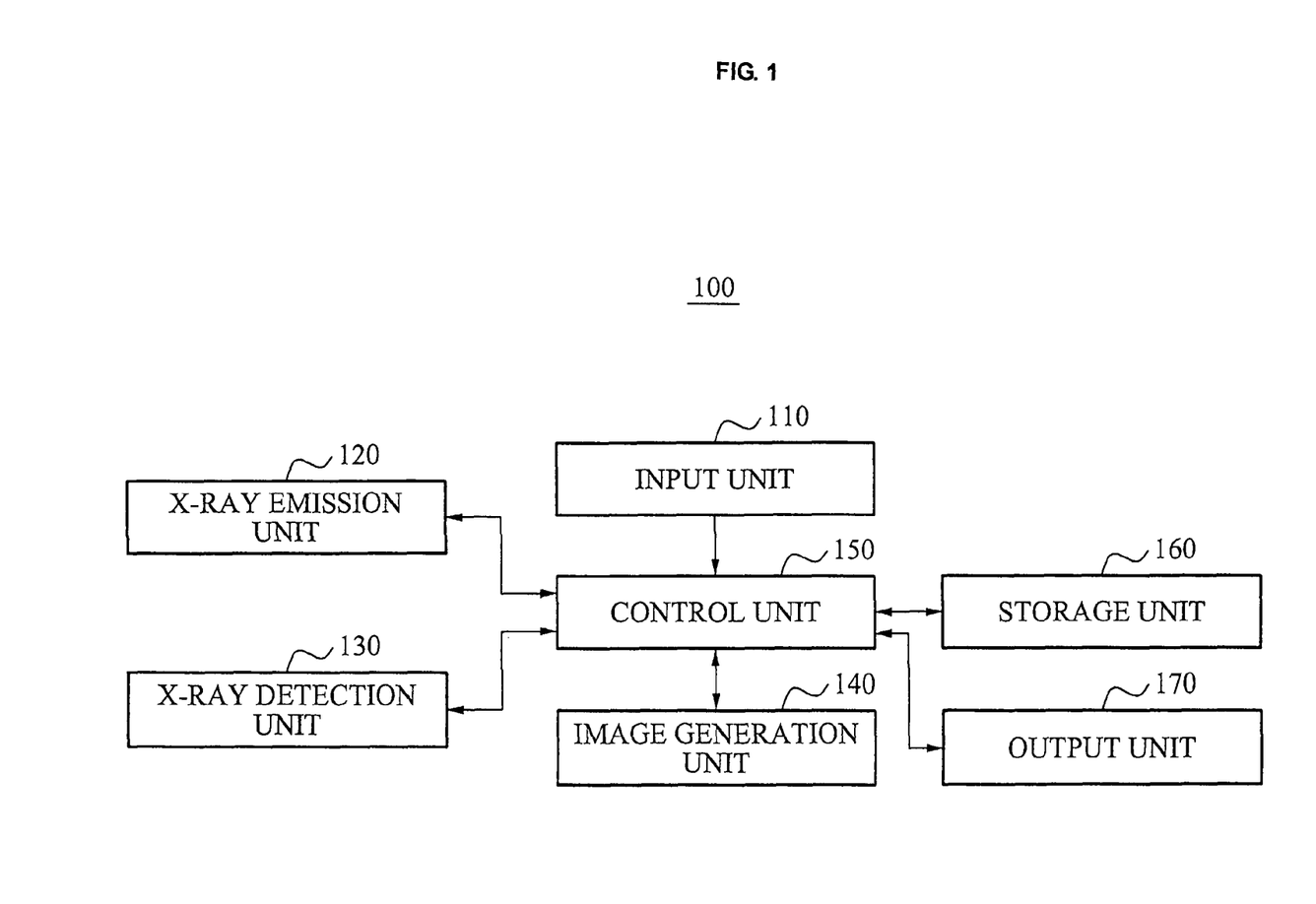
FIG. 1 illustrates a block diagram of a breast imaging apparatus according to one or more embodiments.

FIG. 1 illustrates a block diagram of a breast imaging apparatus according to one or more embodiments. Referring to FIG. 1, the breast imaging apparatus 100 includes an input unit 110, an X-ray emission unit 120, an X-ray detection unit 130, an image generation unit 140, a control unit 150, and a storage unit 160. The breast imaging apparatus 100 may also include an output unit 170 such as a display to display an image or a printer to print an image.

The input unit 110 receives signals corresponding to a doctor or operator's operation of an input device provided at the outside of the breast imaging apparatus 100. For example, in a case where the doctor or operator operates an input device to start breast imaging, the input unit 110 receives a breast imaging signal.

The X-ray emission unit 120 is movable to emit an X-ray to a breast which is an object of examination.

The X-ray emission unit 120 may be disposed at tens of centimeters apart from the breast. The X-ray emission unit 120 emits X-rays from respectively different regions by moving. In addition, the X-ray emission unit 120 may emit the X-rays with different energy spectrums and different doses of irradiation according to regions above which the X-rays are emitted.

The X-ray emission unit 120 emits X-rays of two different energy spectrums from above a first region of the breast which is the examination object. Specifically, the X-ray emission unit 120 emits an X-ray of a first energy spectrum and an X-ray of a second energy spectrum in the first region of the breast. The first region may be a central region of the breast.

The X-ray emission unit 120 may emits the X-rays of the first energy spectrum and the second energy spectrum a plurality of times. The X-ray emission unit 120 may vary its position within the first region every time of emitting the X-rays of the first energy spectrum and the second energy spectrum.

After emitting the X-rays to the breast from above the first region, the X-ray emission unit 120 emits an X-ray of a third energy spectrum from above a second region of the breast, which is different from the first region. A spectrum of the third energy spectrum may be different from or identical to spectrums of the first and the second energy spectrums.

The second region may be an outer region of the central region. Therefore, the X-ray emission unit 120 may emit the X-ray of the third energy spectrum from at least one position within the second region by a plurality of times. The X-ray emission unit 120 may vary its position every time of emitting the X-ray of the third energy spectrum.

After emitting the X-ray to the breast from the second region, the X-ray emission unit 120 may additionally emit X-rays of a fourth energy spectrum and a fifth energy spectrum from at least one position within a third region. Spectrums of the fourth energy spectrum and the fifth energy spectrum may be different from or identical to the spectrums of the first to the third energy spectrums.

The third region may be an outermost area of the breast and may include a region overlapping the second region. The X-ray emission unit 120 may emit the X-ray of the fourth energy spectrum and the X-ray of the fifth energy spectrum at least once, respectively, from any one position within the third region. When both the X-rays of the fourth energy spectrum and the fifth energy spectrum are emitted several times, the X-ray emission unit 120 may vary its position within the third region every time.

Dose of the X-rays emitted by the X-ray emission unit 120 may be varied according to the first, the second, and the third regions of the breast. More specifically, the X-ray emission unit 120 may emit the X-ray of the first energy spectrum from above the first region by a first dose and emit the X-ray of the second energy spectrum from above the first region by a second dose. In this case, the first dose and the second dose may be equal to or different from each other.

The X-ray emission unit 120 may emit the X-ray of the third energy spectrum from above the second region by a third dose. Here, the third dose may be smaller than a sum of the first dose and the second dose. In other words, the X-ray emission unit 120 emits a low dose of the X-ray from above the second region.

In addition, the X-ray emission unit 120 may emit the X-ray of the fourth energy spectrum by a fourth dose and emit the X-ray of the fifth energy spectrum by a fifth dose from the third region. Here, the fourth dose and the fifth dose may be equal to or different from each other. Also, a sum of the fourth dose and the fifth dose may be greater than the third dose and smaller than the sum of the first dose and the second dose. That is, since the X-ray emission unit 120 emits the X-ray from the second region and the third region by a lower dose than the sum of the first and the second doses, the total dose of the X-rays emitted to the breast may be reduced.

Also, the X-ray emission unit 120 is capable of reducing the dose of the X-ray absorbed in a patient's body (breast) by increasing bandwidths of the first energy spectrum and the second energy spectrum of the X-ray emitted from above the first region of the breast.

The X-ray detection unit 130 detects the X-ray emitted from the X-ray emission unit 120 and passed through the breast, thereby generating a plurality of image frames related to the breast. The X-ray detection unit 130 may include a charge coupled device (CCD) camera.

That is, the X-ray detection unit 130 may generate a plurality of image frames by detecting the X-ray emitted from above the first region of the breast and also generate a first image group consisting of the plurality of image frames.

Additionally, the X-ray detection unit 130 may generate a plurality of image frames by detecting the X-ray of the third energy spectrum emitted from above the second region of the breast and also generate a second image group consisting of the plurality of image frames.

Also, the X-ray detection unit 130 may generate a third image group consisting of a plurality of image frames by detecting the X-ray of the fourth energy spectrum and the X-ray of the fifth energy spectrum emitted from above the third region of the breast.

The X-ray detection unit 130 detects the X-ray of the first energy spectrum and the X-ray of the second energy spectrum emitted from above the first region of the breast, thereby generating the plurality of image frames having a full resolution, and generates the first image group consisting of the image frames.

In addition, the X-ray detection unit 130 may detect the X-ray of the third energy spectrum emitted from above the second region and bin the plurality of pixels corresponding to the detected X-ray into one pixel in predetermined pixel units. As a result of the binning, the plurality of image frames constituting the second image group may have a low resolution.

The X-ray detection unit 130 may increase an imaging speed by reducing time to generate the plurality of image frames of the second image group and also increase sensitivity of the plurality of image frames.

The image generation unit 140 generates 3-dimension (3D) image data related to the breast by combining the plurality of image frames constituting each of the first to the third image group generated by the X-ray detection unit 130. In this process, the image generation unit 140 equalizes the plurality of image frames constituting the first image group.

In detail, the image frames of the first image group may have different resolutions and noise characteristics due to the different energy spectrums, that is, the first energy spectrum and the second energy spectrum. To this end, the image frames of the first image group are equalized to have similar or equal resolution or noise characteristics. The equalization may also be performed to the image frames constituting the third image group in the same manner.

The image generation unit 140 generates the 3D image data related to the breast by combining the equalized image frames of the first and the third image groups with the binned image frames of the second image group.

When the breast imaging signal is input to the input unit 110, the control unit 150 controls the operations of the X-ray emission unit 120, the X-ray detection unit 130, and the image generation unit 140 to thereby generate the image data related to the breast. In addition, the control unit 150 stores the generated image data in the storage unit 160.

The breast imaging apparatus 100 may transmit the image data to a display device in electrical connection with the breast imaging apparatus 100. Alternatively, the breast imaging apparatus 100 may further include a display device to display the image data.

Figure 2:
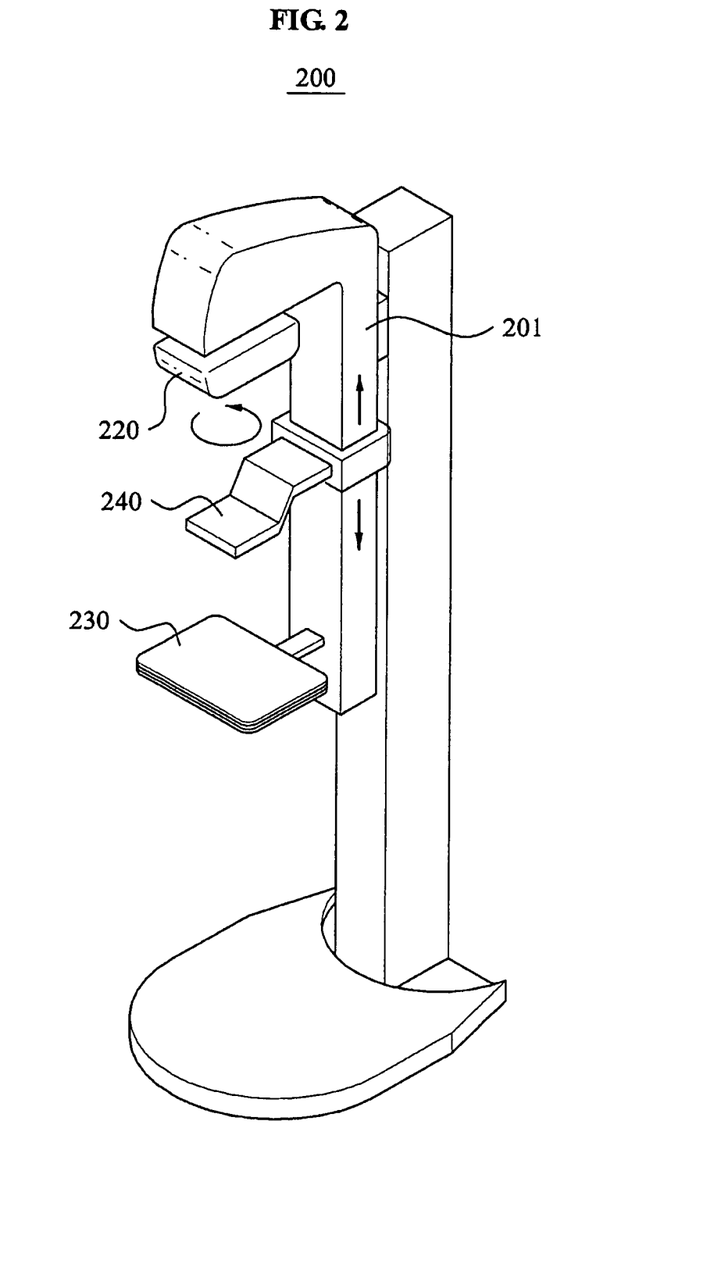
FIG. 2 illustrates a view showing the structure of the breast imaging apparatus according to one or more embodiments.
Figure 3:
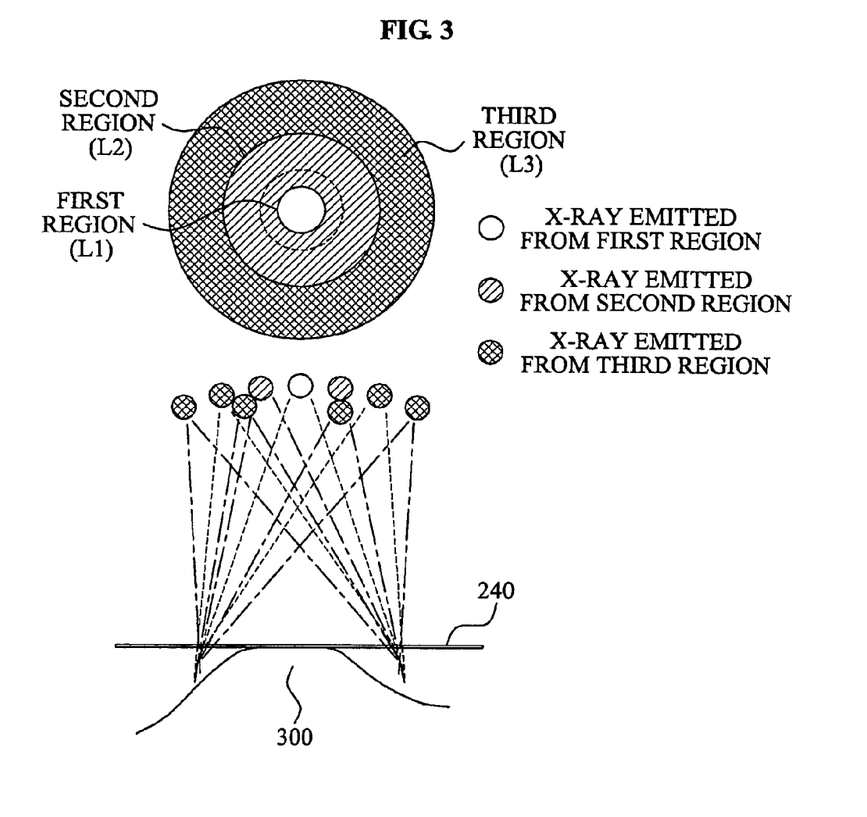
FIG. 3 illustrates a view showing the operations of the breast imaging apparatus according to one or more embodiments.

FIG. 2 is a view illustrating the breast imaging apparatus according to the one or more embodiments. FIG. 3 is a view illustrating the operation of the breast imaging apparatus according to one or more embodiments. FIG. 2 shows the external structure of a breast imaging apparatus 200. The breast imaging apparatus 200 includes an X-ray emission unit 220, a compression plate 240, and an X-ray detection unit 230.

The breast imaging apparatus 200 shown in FIG. 2 is structured such that a patient undergoes breast imaging in a standing position with her breast compressed between the compression plate 240 and the X-ray detection unit 230. However, the external structure of the breast imaging apparatus 200 is not limited as shown in FIG. 2 but may allow the patient to undergo the breast imaging in a sitting position.

The patient, while standing, may undergo the breast imaging with the patient's breast between the compression plate 240 and the X-ray detection unit 230 with her breast compressed. In this case, the breast may be compressed by the compression plate 240 and the X-ray detection unit 230 in an up and down direction, a lateral direction, or a forward and backward direction. A main body 201 of the breast imaging apparatus 200 may be rotated to image the breast in the lateral direction or the forward and backward direction.

In the state where the patient's breast is compressed between the compression plate 240 and the X-ray detection unit 230, a doctor or an operator operates the breast imaging apparatus 200 to start the imaging. Upon starting the imaging operation, the X-ray emission unit 220 emits X-rays of a predetermined energy spectrum from above first, second, and third regions of the breast.

Here, the X-ray emission unit 220 is capable of position change, rotation, and an oblique movement.

As shown in FIG. 3, during the breast imaging, the X-ray emission unit 220 emits the X-rays while moving among the first region L1, the second region L2, and the third region L3 of a breast 300.

The first region L1 may be a central region of the breast 300. The second region L2 may be an outer region of the central region. The third region may be an outermost region of the breast 300. In addition, the third region L3 includes a region from a circle shown by a dotted line in the second region L2 to an outermost circumference of the breast 300. Therefore, the third region L3 may overlap the second region L2. However, the first to the third regions L1 to L3 are not limited as described above.

A plurality of positions belong to the first region to the third region L1 to L3. The X-ray emission unit 220 may emit the X-ray from at least one position of each region.

For example, the X-ray emission unit 220 sequentially emits X-rays of two energy spectrums from at least one position of a first region L1. More specifically, the X-ray emission unit 220 emits the X-ray of the first energy spectrum and then the X-ray of the second energy spectrum from above the first region L1 of the breast 300. Here, however, there is no specific emission order between the X-ray of the first energy spectrum and the X-ray of the second energy spectrum.

After the emission of the X-ray from the first region L1, the X-ray emission unit 220 moves to the second region L2 to emit an X-ray of a third energy spectrum to the breast 300. The X-ray emission unit 220 may emit the X-ray of the third energy spectrum from at least one position within the second region L2 by a plurality of times. In addition, the X-ray emission unit 220 may obliquely move by a predetermined angle (for example, about 5 to 45°) and may also rotate during the X-ray emission.

After the emission of the X-ray from the second region L2, the X-ray emission unit 220 moves to the third region L3 to emit an X-ray of a fourth energy spectrum and an X-ray of a fifth energy spectrum to the breast 300. Here, the X-ray emission unit 200 may emit the X-ray of the fourth energy spectrum and the fifth energy spectrum from at least one position within the third region L3 by a plurality of times. In the same manner as when emitting the X-ray from the second region L2, the X-ray emission unit 220 may have a predetermined emission angle or rotate during the X-ray emission. In this case, there is no specific emission order between the X-ray of the fourth energy spectrum and the X-ray of the fifth energy spectrum.

When the X-ray emission unit 220 emits the X-ray from above any of the first to the third regions L1 to L3, the X-ray may be emitted to the overall region of the breast 300 due to dispersion of the X-ray.

According to the embodiments, the X-ray emission unit 220 may emit the X-rays only from above the first region L1 and the second region L2 while optionally emitting the X-ray from above the third region L3 as necessary. In addition, the X-ray emission unit 220 may emit the X-rays without a specific order among the first to the third regions L1 to L3.

The X-ray emission unit 220 may emit the X-ray of the first energy spectrum by a first dose and the X-ray of the second energy spectrum by a second dose. Also, the X-ray emission unit 220 may emit the X-ray of the third energy spectrum by a third dose. Here, the third dose may be smaller than a sum of the first and the second doses.

In addition, the X-ray emission unit 220 may emit the X-ray of the fourth energy spectrum by a fourth dose and the X-ray of the fifth energy spectrum by a fifth dose. Here, the sum of the fourth and the fifth doses is greater than the third dose and smaller than the sum of the first and the second doses.

The X-ray detection unit 230 detects the X-ray passed through the breast 300, thereby generating a plurality of image frames. The breast imaging apparatus 200 processes each of the image frames and combines the processed image frames, thereby generating image data.

Since the breast imaging apparatus 200 shown in FIG. 2 uses a low dose of X-ray, the image having an improved accuracy of detecting microcalcifications (MC) and masses may be obtained. In diagnosis of a breast cancer through breast imaging, MCs and masses need to be accurately detected through the image. Since the MCs are about 100 to 400 μm in size, a high-resolution imaging technology is needed to detect the MCs. On the other hand, the masses being relatively larger than MCs by having the size of several millimeters do not require the high-resolution imaging technology. However, since the masses have the same components as breast tissues, it is hard to discern the masses from surrounding tissues in the image.

The breast imaging apparatus 200 emits the X-rays of two different energy spectrums from above the first region L1 to the breast 300 and detects the emitted X-rays, thereby generating a plurality of image frames having a full resolution and also generating a first image group by the image frames. Therefore, the image frames constituting the first image group may be used for detection of the MCs which are small. Here, as the breast imaging apparatus 200 emits the X-rays of the two different energy spectrums respectively by the first dose from above the first region L1, the dose of the X-ray being absorbed in the patient's body (breast) may increase. Considering this, the breast imaging apparatus 200 may reduce the dose of the X-ray absorbed in the patient's body (breast) by increasing bandwidths of the first energy spectrum and the second energy spectrum.

In addition, the breast imaging apparatus 200 may generate a second image group by emitting the X-ray of one energy spectrum from above the second region L2 to the breast 300 and detecting the emitted X-ray. When the plurality of image frames are generated by detection of the X-ray emitted from above the second region L2, the breast imaging apparatus 200 bin a plurality of pixels corresponding to the detected X-ray in predetermined pixel units, thereby generating a plurality of image frames having a low resolution. Therefore, sensitivity of the image frames constituting the second image group may increase and, as a result, the masses are discerned from the surrounding breast tissues in the image frames of the second image group. That is, the masses are detected by the second image group. Here, the breast imaging apparatus 200 may emit the X-ray of one energy spectrum from above the second region L2 by the third dose which is smaller than the sum of the first dose and the second dose so that the dose of the X-ray absorbed in the patient's body is reduced.

The breast imaging apparatus 200 may increase an X-ray detection speed by binning the plurality of pixels in units of 2 pixels, 4 pixels, or more in the second region L2.

The breast imaging apparatus 200 may generate a third image group constituting a plurality of image frame having a full resolution by emitting X-rays of different energy spectrums from above the third region L3 and detecting the emitted X-rays. The breast imaging apparatus 200 may obtain information on a depth direction (thickness direction) of small masses by using the plurality of image frames of the third image group.

When the pluralities of the image frames each constituting the first, the second, and the third image groups are generated, the breast imaging apparatus 200 processes and combines the image frames to generate 3D image data related to the breast. In detail, the breast imaging apparatus 200 equalizes the image frames of the first and the third image groups so that resolutions and noise characteristics of the image frames become similar or equal.

In addition, the breast imaging apparatus 200 may log-operates each of the image frames constituting the first image group, apply a weight, and combine the image frames to thereby detect the MCs. Alternatively, the breast imaging apparatus 200 may detect the MCs from the image frames of the first image group by using a substance separation algorithm.

The equalization process and the MC detection process described above may be applied to the image frames of the third image group in the same manner.

The breast imaging apparatus 200 may generate the 3D image data related to the breast by combining the pluralities of the image frames constituting each of the first, the second, and the third image groups. The image frames constituting the first to the third image groups may be totally about 10 to 20 frames. The breast imaging apparatus 200 generates the 3D image data related to the breast by combining those image frames.

The breast imaging apparatus 200 may detect the MCs and the masses more accurately and generate the image data, thereby enabling doctors to more accurately diagnose the breast cancer by using the 3D image data. Furthermore, the X-ray absorbed in the patient's body may be reduced since the low dose of the X-ray is used.

Figure 4:
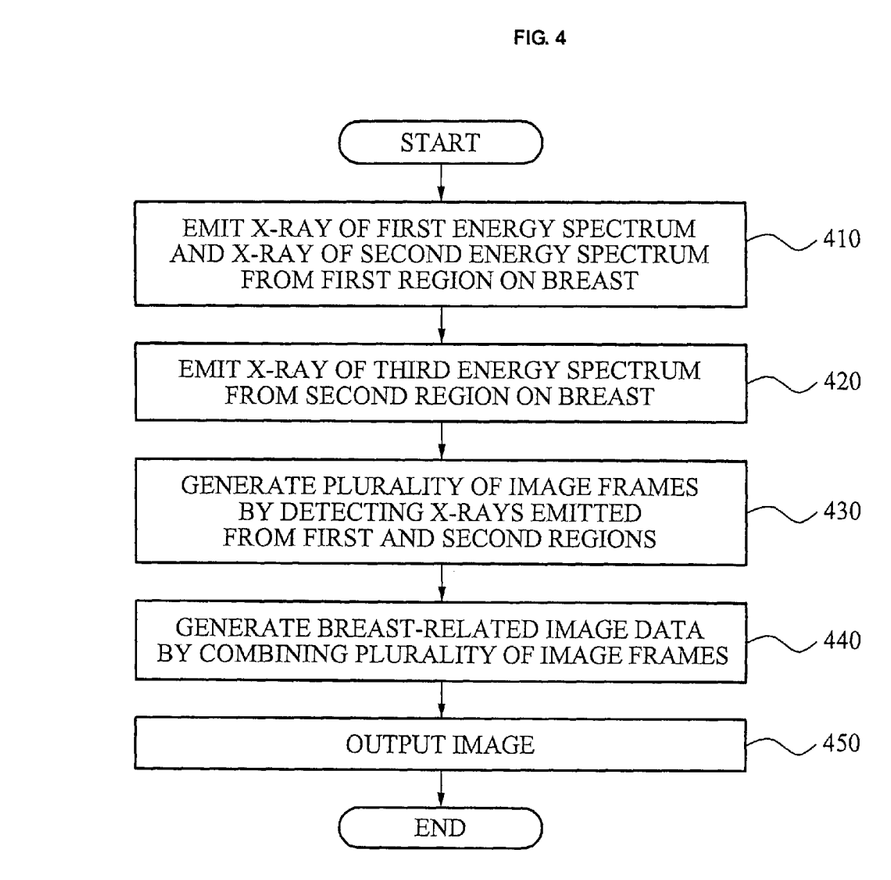
FIG. 4 illustrates a flowchart for explaining a method for imaging a breast according to one or more embodiments.

FIG. 4 is a flowchart for explaining a method for imaging a breast according to the one or more embodiments. Referring to FIG. 4, upon input of the breast imaging signal, the breast imaging apparatuses 100 and 200 emit the X-ray of the first energy spectrum and the X-ray of the second energy spectrum from above the first region of the breast (operation S410). Here, the first energy spectrum and the second energy spectrum may be different from each other. The breast imaging apparatuses 100 and 200 may emit the X-ray of the first energy spectrum and the X-ray of the second energy spectrum from at least one position within the first region by a plurality of times.

The breast imaging apparatuses 100 and 200 emit the X-ray of the third energy spectrum from above the second region of the breast (operation S420). The second region may include different positions from positions of the first region. The third energy spectrum may have a spectrum identical to or different from any one of the first energy spectrum and the second energy spectrum. In addition, the breast imaging apparatuses 100 and 200 may emit the X-ray of the third energy spectrum from at least one position within the second region by a plurality of times.

The breast imaging apparatuses 100 and 200 generate the plurality of image frames related to the breast by detecting the X-rays of the first energy spectrum to the third energy spectrum, emitted to and passed through the breast (operation S430).

The breast imaging apparatuses 100 and 200 generate the image data related to the breast by combining the image frames (operation S440). An image of the breast may be outputted on an output unit 170 such as a display or outputted on a medium by a printer (operation S450) based on the image data.

As described above, the breast imaging apparatuses 100 and 200 are capable of detecting the MCs and the masses more accurately and generating the image data related to the breast, by emitting the X-rays of different energy spectrums from above different regions of the breast which is the examination object.

Figure 5:
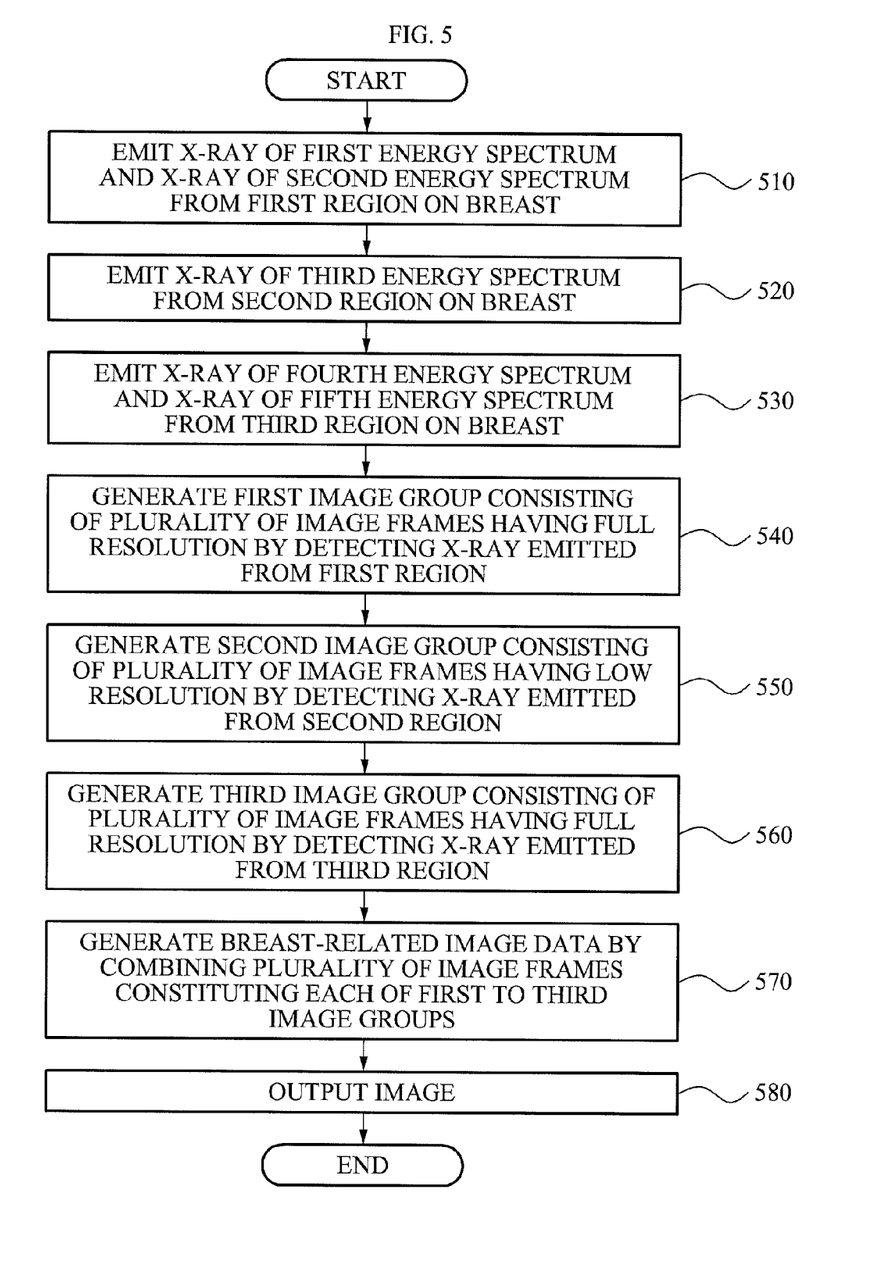
FIG. 5 illustrates a flowchart for explaining a method for imaging a breast according to one or more embodiments.

FIG. 5 is a flowchart for illustrating a breast imaging method according to other one or more embodiments. Referring to FIG. 5, upon input of the breast imaging signal, the breast imaging apparatuses 100 and 200 emit the X-ray of the first energy spectrum and the X-ray of the second energy spectrum from above the first region of the breast (operation S510). Here, the X-ray of the first energy spectrum may be emitted by a first dose and the X-ray of the second energy spectrum may be emitted by a second dose.

The breast imaging apparatuses 100 and 200 emit the X-ray of the third energy spectrum from above the second region which is different from the first region (operation S520). Here, the X-ray of the third energy spectrum may be emitted by a third dose smaller than the sum of the first dose and the second dose.

The breast imaging apparatuses 100 and 200 emit the X-ray of the fourth energy spectrum and the X-ray of the fifth energy spectrum from above the third region (operation S530). Here, the X-ray of the fourth energy spectrum may be emitted by the fourth dose and the X-ray of the fifth energy spectrum may be emitted by the fifth dose. The sum of the fourth and the fifth doses may be greater than the third dose and smaller than the sum of the first dose and the second dose (third dose<sum of the fourth and the fifth doses<sum of the first and the second doses).

The breast imaging apparatuses 100 and 200 detect the X-ray emitted from above the first region and passed through the breast, thereby generating the first image group consisting of the plurality of image frames having the full resolution (operation S540).

Additionally, the breast imaging apparatuses 100 and 200 detect the X-ray emitted from above the second region and passed through the breast, thereby generating the second image group consisting of the plurality of image frames having the low resolution (operation S550). In regard to the X-ray emitted from above the second region and passed through the breast, the breast imaging apparatuses 100 and 200 may bin pixels corresponding to the detected X-ray into one pixel in predetermined pixel units. As a result of the binning process, the breast imaging apparatuses 100 and 200 may generate the image frames of the second image group to have the low resolution.

Also, the breast imaging apparatuses 100 and 200 detect the X-ray emitted from above the third region and passed through the breast, thereby generating the third image group consisting of the image frames having the full resolution (operation S560).

Although the operations S510 through S560 have been explained to be sequentially performed, there is no specific order among the operations S510 through S560. The operations S540 through S560 may be performed simultaneously with emission of the X-ray in corresponding to regions. For example, it is exemplary that, while operation S510 that emits the X-ray from above the first region is being performed, operation S540 that detects the X-ray emitted from above the first region may be simultaneously performed.

The breast imaging apparatuses 100 and 200 generate the image data related to the breast by combining the image frames constituting each of the first image group to the third image group (operation S570). For this, the breast imaging apparatuses 100 and 200 may equalize the image frame of the first and the third image groups and then combine the equalized image frames with the image frames of the second image group.

An image of the breast may be outputted on an output unit 170 such as a display or outputted on a medium by a printer (operation S580) based on the image data.

As described above, the breast imaging apparatuses 100 and 200 are capable of generating image data in which the MCs and the masse are accurately detected, by using a low dose of X-ray irradiation.

The methods according to the above-described embodiments may be recorded in non-transitory computer-readable media including computer readable instructions such as a computer program to implement various operations by executing computer readable instructions to control one or more processors, which are part of a general purpose computer, a computing device, a computer system, or a network. The media may also have recorded thereon, alone or in combination with computer readable instructions, data files, data structures, and the like. The computer readable instructions recorded on the media may be those specially designed and constructed for the purposes of embodiments, or they may be of the kind well-known and available to those having skill in the computer software arts. The computer-readable media may also be embodied in at least one application specific integrated circuit (ASIC) or Field Programmable Gate Array (FPGA), which executes (processes like a processor) computer readable instructions. Examples of non-transitory computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The media may be transfer media such as optical lines, metal lines, or waveguides including a carrier wave for transmitting a signal designating the program command and the data construction. Examples of computer readable instructions include both machine code, such as produced by a compiler, and files containing higher level code that may be executed by the computer using an interpreter. The described hardware devices may be configured to act as one or more software modules in order to perform the operations of the above-described embodiments, or vice versa. Another example of media may also be a distributed network, so that the computer readable instructions are stored and executed in a distributed fashion.

Although embodiments have been shown and described, it would be appreciated by those skilled in the art that changes may be made in these embodiments without departing from the principles and spirit of the disclosure, the scope of which is defined in the claims and their equivalents.

What is claimed is:

1. An apparatus for imaging a breast, comprising:
   an X-ray emission unit that emits an X-ray of a first energy spectrum and an X-ray of a second energy spectrum from above a first region of a breast and that emits an X-ray of a third energy spectrum from above a second region of the breast different from the first region of the breast;
   an X-ray detection unit that generates a first image group consisting of a plurality of image frames having a first resolution by detecting X-rays of the first energy spectrum and the second energy spectrum and generates a second image group consisting of a plurality of image frames having a second resolution by detecting the X-ray of the third energy spectrum; and
   an image generation unit that generates image data related to the breast by combining the plurality of image frames of the first image group and the second image group,
   wherein each of the first energy spectrum, the second energy spectrum and the third energy spectrum is different, and
   wherein the first resolution is higher than the second resolution.

2. The apparatus of claim 1, wherein the X-ray emission unit further emits an X-ray of a fourth energy spectrum and a fifth energy spectrum from above a third region of the breast which is different from the first region of the breast.

3. The apparatus of claim 2, wherein the second region of the breast and the third region of the breast share an overlapping region.

4. The apparatus of claim 2, wherein the first resolution is a full resolution.

5. The apparatus of claim 4, wherein the X-ray detection unit generates the second image group consisting of the plurality of image frames having the second resolution by binning a plurality of pixels corresponding to the X-ray of the third energy spectrum emitted from above the second region of the breast, and wherein the second resolution is a low resolution.

6. The apparatus of claim 5, wherein the X-ray detection unit generates a third image group consisting of a plurality of image frames having a full resolution by detecting the X-rays of the fourth energy spectrum and the fifth energy spectrum emitted from above the third region of the breast.

7. The apparatus of claim 6, wherein the image generation unit generates image data related to the breast by combining the plurality of image frames constituting each of the first group, the second group, and the third group generated in the X-ray detection unit.

8. The apparatus of claim 1, wherein the apparatus further comprises an output unit to output image of the breast based on the image data.

9. The apparatus of claim 8, wherein the output unit is a display unit which displays the image of the breast.

10. The apparatus of claim 8, wherein the output unit is a printer, which prints the image of the breast.

11. The apparatus of claim 1, wherein an emission angle of each of the X-rays of the first energy spectrum and the second energy spectrum is different.

12. A method for imaging a breast, comprising:
    emitting X-rays of a first energy spectrum and a second energy spectrum from above a first region of a breast;
    emitting an X-ray of a third energy spectrum from above a second region of the breast different from the first region of the breast;
    generating a first image group consisting of a plurality of image frames having a first resolution by detecting the X-rays of the first energy spectrum and the second energy spectrum;
    generating a second image group consisting of a plurality of image frames having a second resolution by detecting the X-ray of the third energy spectrum; and
    generating image data related to the breast by combining the plurality of image frames of the first image group and the second image group,
    wherein each of the first energy spectrum, the second energy spectrum and the third energy spectrum is different, and
    wherein the first resolution is higher than the second resolution.

13. The method of claim 12, further comprising:
    emitting X-rays of a fourth energy spectrum and a fifth energy spectrum from above a third region of the breast, which is different from the first region of the breast.

14. The method of claim 13, wherein the second region of the breast and the third region breast share an overlapping region.

15. The method of claim 13, further comprising:
    generating a third image group consisting of a plurality of image frames having a full resolution by detecting X-rays of the fourth energy spectrum and the fifth energy spectrum emitted from above the third region of the breast.

16. The method of claim 15, wherein the generating of the image data related to the breast comprises:
    generating image data related to the breast by combining the plurality of image frames constituting each of the first image group, the second image group, and the third image group.

17. The method of claim 13, wherein the generating the second image group comprises:
    generating the second image group consisting of a plurality of image frames having the low resolution by binning a plurality of pixels corresponding to the X-ray of the third energy spectrum emitted from above the second region of the breast,
    wherein the second resolution is a low resolution.

18. The method of claim 13, wherein an emission angle of each of the X-rays of the first energy spectrum and the second energy spectrum is different.

19. The method of claim 12, wherein the method further comprises outputting an output image of the breast based on the image data.

20. The method of claim 19, wherein the method further comprises displaying the output image of the breast is on a display unit.

21. The method of claim 19, wherein the method further comprises printing the output image of the breast using a printer.

22. At least one non-transitory computer readable recording medium storing computer readable instructions that control at least one processor to implement the method of claim 12.

* * * * *